(12) United States Patent
Friedrich et al.

(10) Patent No.: US 6,385,380 B1
(45) Date of Patent: May 7, 2002

(54) HOLLOW OPTICAL WAVEGUIDE FOR TRACE ANALYSIS IN AQUEOUS SOLUTIONS

(75) Inventors: Karl Friedrich, Friedberg; Peter Dress, Bruchsal, both of (DE); Mathias Belz, Sarasota, FL (US)

(73) Assignee: World Precision Instruments, Inc., Sarasota, FL (US)

( * ) Notice: Subject to any disclaimer, the term of this patent is extended or adjusted under 35 U.S.C. 154(b) by 0 days.

(21) Appl. No.: 09/294,686

(22) Filed: Apr. 19, 1999

(30) Foreign Application Priority Data

Apr. 21, 1998 (DE) .......................................... 198 17 738

(51) Int. Cl.$^7$ ................................................. G02B 6/02

(52) U.S. Cl. ........................... 385/125; 385/13; 356/432

(58) Field of Search .............................. 385/125, 126, 385/12, 13; 250/227; 73/61.4 A; 356/246, 73, 301, 432, 436, 244, 440, 133

(56) References Cited

U.S. PATENT DOCUMENTS

| | | | | |
|---|---|---|---|---|
| 4,504,114 A | * | 3/1985 | Arrington | 350/96.34 |
| 4,802,761 A | * | 2/1989 | Bowen et al. | 356/301 |
| 5,184,192 A | * | 2/1993 | Gilby et al. | 356/246 |
| 5,521,703 A | * | 5/1996 | Mitchell | 356/301 |
| 6,016,372 A | * | 1/2000 | Fein et al. | 385/12 |

\* cited by examiner

Primary Examiner—Cassandra Spyrou
Assistant Examiner—Euncha Cherry
(74) Attorney, Agent, or Firm—Alix, Yale & Ristas, LLP (57) ABSTRACT

Low concentrations of substances dissolved in liquids are detected by coupling analysis/excitation light into the liquid core of an optical waveguide in the form of a capillary. When the substance of interest is to be excited to cause the emission of fluorescent light, the excitation light is transversely coupled into the hollow core of the waveguide and the generated fluorescent light is kept in the optical path of the waveguide for as long as possible. The invention also contemplates the use, in either an absorption or fluorescence mode, of specially treated fused silica fibers to deliver analysis/excitation light with very short wavelengths into the liquid core of an optical waveguide.

16 Claims, 6 Drawing Sheets

HOLLOW OPTICAL WAVEGUIDE FOR TRACE ANALYSIS IN AQUEOUS SOLUTIONS

BACKGROUND OF THE INVENTION

1. Field of the Invention

The present invention relates to the detection of low concentrations of dissolved materials in solvents and, particularly, to optical analysis procedures which may be performed in a continuous manner. More specifically, this invention is directed to improvements in sensors comprising hollow optical waveguides and, especially, to liquid core waveguide sensors with enhancements in the means for delivery of analysis/excitation light to the core liquid. Accordingly, the general objects of the present invention are to provide novel and improved methods and apparatus of such character.

2. Description of the Prior Art

It is known to analyze fluids in cuvettes formed from optically transparent material, usually quartz, which have been drawn into the form of cylindrical, thin-walled capillaries. The fluid to be analyzed is confined in the capillary, i.e., forms a liquid core. Materials dissolved in such a confined liquid core can, even at low concentrations, be detected due to their characteristic optical absorbance of analysis light, their characteristic fluorescence when excited by analysis light of the appropriate wavelength or their Raman spectra. The coupling of light into and out of a capillary employed in such prior art analysis procedures has usually been accomplished at the opposite end faces of the capillary with the analysis light being directed through the cuvette axially thereof. The solvent with dissolved compounds is customarily delivered to and exhausted from the cuvette via radially oriented liquid channels.

It is also known, in the interest of limiting light leaving a cuvette in directions transverse to the axis thereof, to employ a coating on the inner wall of the capillary. When such a coating has a refractive index which is lower than that of the commonly used solvents in the visible and ultraviolet wavelength spectra, total light reflection will occur at the liquid/coating interface. This reflection decreases light loss in the liquid core and longer optical path lengths, which increase the sensitivity of a sensor cell comprising such a liquid core waveguide, are thus possible. The coating on the inner wall of the capillary, where the core liquid is to be an aqueous solution, will preferably consist of an amorphous fluorinated polymer, such as Teflon AF 1600 or Teflon AF 2400. These coating materials respectively have refractive indices of 1.31 and 1.29 in the wavelength region of the sodium-D-line.

The ultraviolet, visible and infrared regions of the light spectrum have long been used in spectroscopy for liquid and gas analysis. Commonly used analysis methods are transmittance and, as noted above, absorbance and fluorescence. To accomplish the desired measurements employing these methods, liquid filled cuvettes are positioned in the path of analysis light generated by an appropriate source. In addition, as disclosed in U.S. Pat. No. 4,260,257, rotational symmetric liquid-flushed, flow-through cells, with small diameters to reduce the sample volume, have been proposed for liquid and gas analysis.

Fiber optics have been developed and improved in recent years, and fiber optic coupling between light sources and cuvettes and flow-through cells has been accomplished. Thus, light from a source may be efficiently coupled into a fiber optic element, consisting of either a single fiber or a fiber bundle, and transmitted thereby into or away from a cuvette. The fibers employed for such purposes preferably consist of glass or quartz, depending on the wavelength of the light to be guided. Light emitted from the end of a fiber optic element, within the angle dictated by the numerical aperture thereof, may be converted by a micro-lens into parallel light which is guided through a cuvette. After such light passes through the relatively short optical path length of a standard cuvette, typically 10 cm, the light is coupled, by means of a focusing lens, into a fiber optic element connected to a light detector. The light detector may be a wavelength-selective system, e.g., a polychromator, or a detector, e.g., a silicon photo-diode, or a photomultiplier tube which may be provided with an analyte-adapted narrow or broad-band optical filter.

In the interest of signal enhancement, quartz and glass tubes with small outer diameters and thin walls, so-called capillaries, have been used as flow-through cells. The choice of quartz and glass tubes, in part, has been based upon the fact that such tubes are chemically inert against many liquids and solvents. These capillaries can be provided with an internal, and possibly also an external, metal coating in an environment where there would be negligible corrosion. However, metal-coated capillaries have the disadvantage of high light loss. Thus, the optical path length is relatively small for a pre-defined signal-to-noise ratio.

As noted above, by providing an optically transparent capillary with a coating of a suitable amorphous fluorinated polymer, an efficient liquid core optical waveguide may be produced. On this point, the following references may be taken into consideration: "Optical Characteristics of Teflon AF Fluoroplastic Materials", by J. H. Lowry et al, Optical Engineering, Volume 31, page 1982 (1992); U.S. Pat. No. 5,184,192; "Raising the Sensitivity Benchmark in Diode Array Detection with Optical Improvements", by P. DeLand, Internat. Laboratory 12C–12H (July 1998); "A Cylindrical Liquid Core Waveguide", by P. Dress et al, Appl. Phys. B63, page 12 (1996) and U.S. Pat. No. 5,570,447. By insuring that the liquid core has a higher refractive index than a coaxial layer of material, as discussed above, coupled light is mainly guided in the liquid core because of the total reflection which occurs at, for example, the liquid/coating interface. In other words, optical losses resulting from transverse emission through the wall of the capillary are substantially eliminated through the use of low refractive index amorphous fluorinated polymers. Liquid core waveguides of the type described, wherein the low refractive index polymer forms either an interior or an exterior coating on the capillary, or forms the capillary itself, can be used as absorption sensors with high resolution. In such absorption sensors, light is axially coupled into and out of the capillary at the end face(s). Such light coupling has typically been accomplished by utilizing some type of focusing device between the light source and the capillary.

The problems concerned with transmission of light at wavelengths below 250 nm has been discussed in the article "UV-stabilized silica based fiber for applications around 200 nm wavelength", by K.-F. Klein et al., Sensors and Actuators B, Vol. 39–123, 305–309 (1997). This article suggests that optical fibers capable of stable transmission of light with wavelengths below 250 nm would allow the field of fiber optic applications to be significantly expanded. For example, field-usable sensors for water pollution by detection of nitrate, nitrite and residual chlorine, which have strong absorption bands below 250 nm, have long been needed.

The principals of capillary-like coated liquid core waveguides have been surveyed in the articled entitled "Capillary Waveguide Sensors", by O. S. Wolfbeis, Anal.

Chem, Vol. 15, page 225 (1996). Side illumination of optical waveguides has also been previously suggested. The sensoric properties of such a side illuminated light guide are based on chemical or physical changes in its specific inner coating by the influence of the detectible substance. These changes include the fluorescence excitation of the inner coating by detectible substances. In such case, advantage is taken of the fact that the magnitude and spectral composition of a fluorescence signal changes with the detectible substances diffusing in and out of the coating. In such a sensor, the generated fluorescent light would be detected at the end of a short capillary.

A disadvantage of the conventional technique of axial coupling of light into a liquid core optical waveguide resides in the fact that the lowest detectible concentration of a substance dissolved in a liquid scales within the effective optical path length of the light to be collected and analyzed in the liquid. An additional disadvantage of axial light in-coupling resides in the fact that, if the optical characteristic to be measured is fluorescence, it becomes difficult to distinguish between the fluorescent light of interest as generated in the core and the analysis/excitation traveling through the core light since both types of light are guided to the end(s) of the waveguide and, accordingly, are simultaneously incident on the collector.

SUMMARY OF THE INVENTION

The present invention provides a sensor, based upon a liquid core optical waveguide, which increases the detection limit, of dissolved substances in fluids at acceptable apparatus dimensions. A sensor in accordance with the invention permits on-line analysis whereby "continuous" detection of a substance in a flow can be accomplished. The invention also encompasses a novel and improved method of trace analysis which employs a hollow optical waveguide. The invention further encompasses the use, particularly for fluorescence applications, of analysis/excitation light with wavelengths less than 230 nm.

In accordance with a preferred embodiment of the invention, trace analysis by measuring fluorescence is accomplished by transversely coupling analysis/excitation light into the liquid core of a hollow optical waveguide having an amorphous fluorinated polymer/core liquid interface. When operated in the fluorescence mode, for water analysis in the wavelength region below 250 nm, for example, an inner coating of Teflon AF on a transparent capillary yields both a very high transmission of analysis light into the waveguide and total reflection of a significant amount of the excited fluorescence light. The performance of the preferred embodiment of the invention can be enhanced, and the problem of absorption in the fiber optic elements used for excitation light input and light output may be overcome, by the employment of UV-stabilized fused silica fibers, especially hydrogen doped fused silica fibers, for coupling excitation light from the source into the waveguide and/or for collection of emitted fluorescence.

Applicants have also found that, in the case of a flow-through cell, sensitivity is maximized if the flow is as laminar as possible in the measurement region thereby avoiding disturbance of the total reflection at the interface between the flowing liquid core and the capillary. Such laminar flow in the measurement region can be realized by maintaining appropriate distances between the opposite ends of the measurement zone, i.e., the areas where light is coupled into and out of the cell, and the channels or conduits through which the core liquid flows into and out of the capillary. Restated, in accordance with the invention, the length of the measurement zone is less than that of the liquid flow path within the waveguide.

Applicants have also discovered that transverse coupling of excitation light, in combination with the light guiding property of the combination of a core liquid with a relatively high optical refractive index and a coaxial lower refractive index capillary, provides a three dimensional separation between in-coupled excitation light and the generated fluorescence light because the excitation light is not directed into the waveguide with an angle which is within the guiding properties of the waveguide. This three dimensional separation permits employment of a stretched, cylindrical waveguide wherein the emitted fluorescence light is guided inside the waveguide and can be detected at both end faces of the capillary.

An advantageous increase in the sensitivity of fluorescence sensors in accordance with the invention results from an increase of the total excitation light flux coupled into the liquid waveguide core region, i.e., increased excitation light intensity causes an increase of the generated fluorescence signal. To increase the excitation light input, in one embodiment of the invention, a line-formed array of fiber optic elements is employed with the individual optical fibers being oriented generally radially with respect to the liquid core waveguide and the array extending longitudinally with respect to the waveguide.

In order to decrease coupling losses at the interface between an individual fiber optic element employed for excitation light transmission and the exterior of the waveguide, a waveguide sensor in accordance with the invention will preferably be modified to present a flat surface which is complementary to the end of the fiber optic element. The flat surface on the waveguide may be provided by grinding the exterior of a cylindrical capillary or by fabricating the capillary as a rectangular tube, i.e., a quadratic liquid core waveguide is employed. In the case of grinding flats on the exterior of the cylindrical waveguide, anti-tangential grinding will increase the optical path length/absorption length of the excitation light by causing at least some of such light to undergo multiple reflections within the waveguide.

A hollow optical waveguide sensor in accordance with the invention may, in the interest of avoiding any deleterious effects of stray light, be surrounded by a reflective metal coating except in the areas where excitation light is to be transversely coupled into the waveguide.

In accordance with a further embodiment of the invention, a cylindrical light source oriented parallel with respect to the axis of a liquid core waveguide is utilized and the light provided by such source is focused by cylindrical lenses into the core of the waveguide.

In accordance with yet another embodiment of the invention, the waveguide comprises a thin, flexible coating, with a refractive index lower than that of the intended core liquid, is employed on a flexible capillary. Alternatively, a flexible waveguide comprised entirely of an amorphous fluorinated polymer, such as Teflon AF, may be utilized. In either case, the flexible waveguide is wrapped around a bar-shaped light source. Such an arrangement is particularly useful for excitation with light in the ultraviolet region.

The present invention is particularly well suited for on-line analysis, particularly a "continuous" measurement process, wherein fluorescence is the optical characteristic of interest. In the past, on-line analysis employing fluorescence measurements has been difficult. The present invention reduces or removes sources of possible reduction of the signal of interest through use of pumps, valves and, if necessary, storage containers. In the case of on-line or continuous analysis, the present invention contemplates selectively and temporarily separating the liquid core waveguide hydraulically from the remaining circulation to enable the excited core liquid to remain in place for a sufficient time for measurement of emitted fluorescent light or sufficient time for shifted absorption of different states of the substance of interest.

To summarize the advantages of the present invention, the sensitivity and detection limit of a sensor employing a liquid core optical waveguide is increased vis-a-vis the prior art. The apparatus and methods of the invention enable the on-line analysis of liquids by the employment of micropumps, valves and storage tanks. In the fluorescence measurement mode, a three-dimensional separation of transverse coupled excitation light and the stimulated fluorescent light is achieved and the fluorescent light to be analyzed may be collected at both end faces of the liquid core waveguide.

The present invention, through analysis of fluorescence produced as a result of UV excitation, permits the use of liquid core waveguides with measurement or optical path lengths in excess of 20 m. The foregoing is possible because the self-absorption of the fluorescent light by shifting to longer wavelengths can be neglected for low analyte concentrations. Also, through the use of specially doped UV stabilized fiber optic elements, particularly hydrogen doped elements, in combination with a coaxial Teflon AF layer on a hollow optical waveguide, fluorescence excitation with light at wavelengths below 250 nm, and particulary as short as 200 nm, is possible.

Through the employment of flexible liquid core waveguides, particularly waveguides comprised of Teflon AF tubing, sensor cells which may be caused to conform to the shape of light sources of various forms, particularly bar-formed lights, are possible. The possibility of using various light sources in the commonly found bar-formed shape permits excitation light to be coupled wavelength selectively into the waveguide, via a linear array of fiber optic elements arranged along the longitudinal axis of the waveguide, for example, and the stimulated fluorescence light can be detected and simultaneously resolved into its spectral components with, again by way of example, a polychromator.

In the practice of the present invention, in either the absorption or fluorescence mode, by employing fiber optic elements with a low water content in combination with core materials having a low water content, the measurement range can be extended to the visible and near infrared region of the light spectrum up to wavelengths of 2.3 $\mu$m. Further, flexible optical fibers can be employed for the fiber optic excitation light transmission and/or fluorescent light collection elements. For example, it is possible to employ fibers comprised of silicate glasses from 380 to 1100 nm, fibers made of PMMA (acrylic) from 350 to 750 nm and fibers comprised of fluorinated polymers from 400 to 1600 nm.

BRIEF DESCRIPTION OF THE DRAWINGS

The present invention may be better understood, and its numerous objects and advantages will become apparent to those skilled in the art, by reference to the accompanying drawings, wherein like reference numerals refer to like elements in the several figures and in which.

DESCRIPTION OF THE DISCLOSED EMBODIMENTS

Figure 1A:
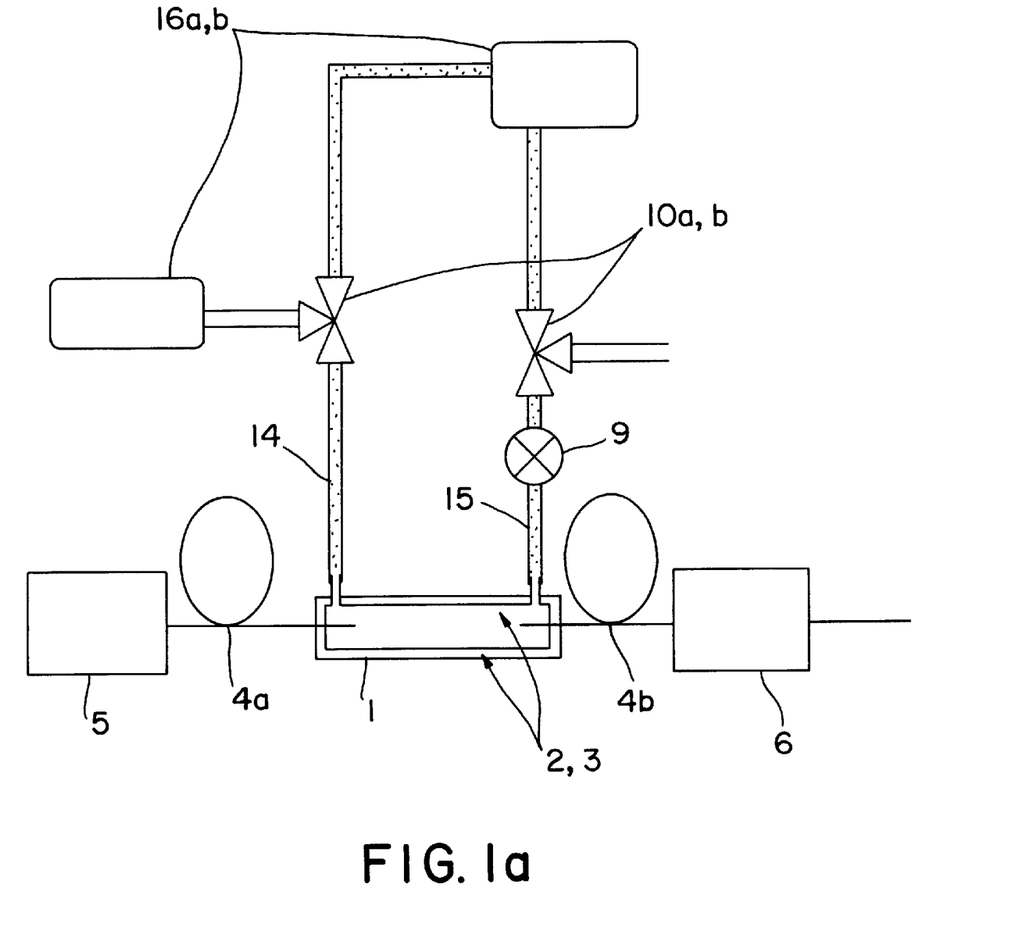
FIG. 1a schematically represents the implementation of an absorption measuring procedure employing a liquid core optical waveguide in accordance with the invention.

FIG. 1a schematically represents the use of a first embodiment of the invention to detect an analyte by means of absorbance. The liquid core waveguide 1 comprises a cylindrical capillary 2 formed from glass or fused silica. The capillary 2 is provided with an inner coating 3 which, when the analyte is in an aqueous solution, is preferably comprised of Teflon AF. The source of analysis light 5, in an absorption application, preferably comprises a UV-light emitting deuterium lamp. Light source 5 is coupled to the waveguide core region, i.e., the analysis light is transmitted, via a fiber optic element 4a. In the FIG. 1a embodiment, the fiber optic element 4a consists of either a single fiber or bundle of fibers formed from hydrogen doped synthetic fused silica. Accordingly, analysis light having wavelengths as short as 180 nm may be utilized. Fiber optic element 4a passes through an end face of the capillary 2, i.e., extends into the liquid core of the waveguide, and is substantially coaxial with the capillary 2. The placement of the end of element 4a within waveguide 1 is an important feature of the FIG. 1a embodiment, as will be described below, in that it permits on-line measurements. At the opposite end face of the liquid core waveguide, the attenuated analysis light is collected and guided to a detector 6 by a further fiber optic element 4b. Collector-fiber element 4b also extends into the core liquid for the reason to be discussed below. Detector 6 may include a polychromator. The arrangement depicted in FIG. 1a may be used to detect nitrate, nitrite and residual chlorine pollution.

The function of the supply and discharge conduits 14 and 15, control valves 10a and 10b, pump 9 and storage containers 16a and 16b will be described below in the discussion of FIG. 1b.

Figure 1B:
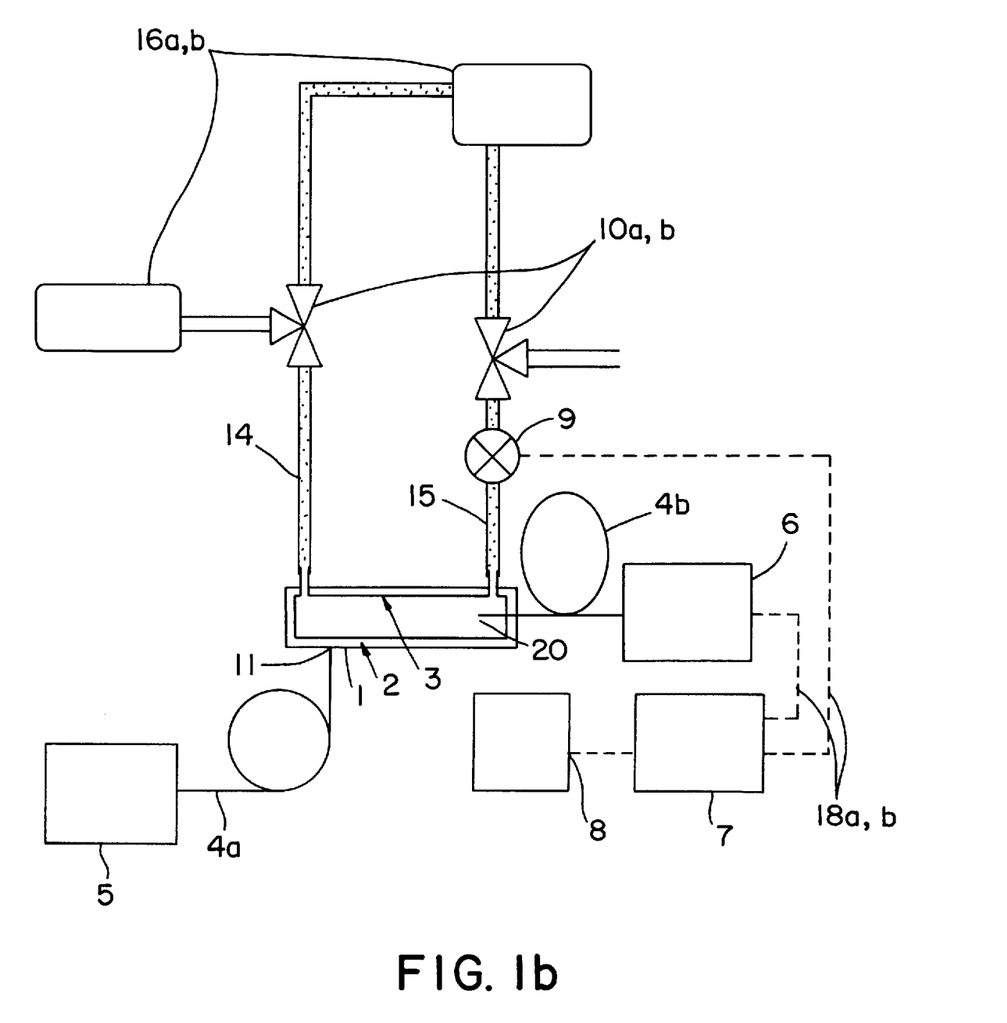
FIG. 1b is a schematic representation, similar to FIG. 1a, depicting the practice of the present invention in a fluorescence measurement mode with transverse delivery of excitation light.

FIG. 1b depicts the use of apparatus in accordance with a second embodiment of the present invention to detect dissolved materials in a solvent by means of measuring the fluorescence produced when such materials are excited by analysis light injected into the a, waveguide. In the FIG. 1b embodiment, the light from source 5 is coupled into the liquid core waveguide 1 from the side, i.e., the light is injected transversely with respect to a plain in which the axis of the waveguide lies. The coupling area 11, i.e., the interface between the end of the fiber optic element 4a and the exterior of the capillary 2 comprising waveguide 1, is displaced from the conduits 14 and 15 for the reason to be described below. Fluorescent light which is caused to be emitted by the excitation of dissolved material in the liquid core of the waveguide is collected in the region 20 and coupled out of the waveguide via fiber optic element 4b. The collected fluorescent light is delivered to detector 6 which provides an electrical signal to an analog-to-digital converter 7. The output of converter 7 is delivered to a computer 8.

An important aspect of the embodiments of FIGS. 1a and 1b is the placement of the area where the analysis/excitation light is coupled into waveguide 1 and the placement of the point of collection of attenuated analysis light or collection of the excited fluorescence. In FIG. 1a, the in-coupling area is the end of fiber optic element 4a. In FIG. 1b, the in-coupling area 11 is the interface between fiber optic element 4a and the side of waveguide 1. In both of FIGS. 1a and 1b, the light to be analyzed is collected at the end of fiber optic element 4b which is immersed in the liquid core of waveguide 1. Applicants have found that significantly improved measurement results are obtained by locating both the in-coupling and collection areas in that portion of the waveguide where the flow of core liquid will be laminar when the sensor is used on-line. Thus, in both embodiments being discussed, the in-coupling area is downstream of the supply conduit 14, thus avoiding turbulence produced at the junction of the supply conduit and waveguide core region. Also, in both embodiments, the end of fiber optic element 4b will be located upstream of the discharge conduit 15, thereby avoiding the region of turbulence associated with the core liquid exiting the waveguide core region.

In the embodiments of FIGS. 1a and 1b, the containers 16a and 16b are employed if the system is to be employed to perform on-line, i.e., continuous, measurements. In such case, the liquid to be analyzed will flow from container 16a into the core region of waveguide 1 via a three-way microvalve 10a. The use of valves 10a and 10b, respectively in the inflow and discharge conduits, allows the test solution to be maintained in waveguide 1 for analysis of long-lived fluorescence light emitting states (FIG. 1b). Flow through the system is produced by means of the pump 9. Solution which has been analyzed is pumped out of waveguide 1 by pump 9 and delivered, via valve 10b, to container 16b. Distilled water may be supplied via conduit 15 and valve 10b for purposes of cleaning waveguide 1. The valves 10a and 10b and the pump 9 will optimally be computer controlled.

The waveguides 1 of the embodiments of FIGS. 1a and 1b are substantially the same. The waveguide of FIG. 1b is shown on an enlarged scale in FIG. 2. In the embodiments being described, the primary components of waveguide 1 are an optically clear glass or quartz capillary 2 and an amorphous fluorinated polymer interior coating 3. In the fluorescence application of FIG. 1b, the light from source 5, preferably UV-light, is transverse coupled via fiber optic element 4a into the waveguide 1. Transverse coupling dictates that the material comprising capillary 2 and its internal coating 3 be selected such that a high degree of transmission of the excitation light from source 5 is guaranteed. In accordance with one aspect of the invention, the fiber optic elements 4a and 4b are preferably comprised of UV-stabilized glass or fused silica fibers of type UVI. To achieve an excitation wavelength which is independent of the excitation volume, it may be desirable to employ a mode mixing element between light source 5 and the discharge end of fiber optic element 4a.

In a particularly useful application of the present invention, the wavelength of the excitation light is in the range of 250 nm to 2500 nm and one or both of the fiber optic elements 4a and 4b comprise fused silica fibers with an undoped core and a fluorine doped cladding. In another application, the wavelength of the excitation light is the range of 180 nm to 1050 nm and the fiber optic elements comprise hydrogen doped fused silica. When the excitation light is in the wavelength range of between 400 to 700 nm, the fiber optic elements preferably comprise polymer-optical fibers (PMMA). When the excitation light is in the wavelength range of between 380 to 1100 nm, the fiber optic elements can be comprised of silicate or other glass. For excitation with light selected from a broad range of wavelengths, i.e., 400 to 1600 nm, it is possible to employ fiber optical elements formed from fluorinated polymers.

The source 5 of excitation light may, depending upon the particular application, comprise a hollow cathode, a filament or discharge lamp, semi-conductor light emitting diodes, an Excimer laser, gas or solid state laser diodes, black radiators and deuterium lamps.

In the practice of the present invention, the capillary 2 of the liquid core waveguide 1 will have an inner diameter in the range of 50 $\mu$m to 5 mm, preferably 200 $\mu$m to 1500 $\mu$m. It is essential, in the embodiments depicted in FIGS. 1a and 1b wherein an optically clear capillary with an internal coating is employed, that the internal coating 3 of waveguide 1 has a refractive index which is smaller than the refractive index of the core liquid.

Figure 2:
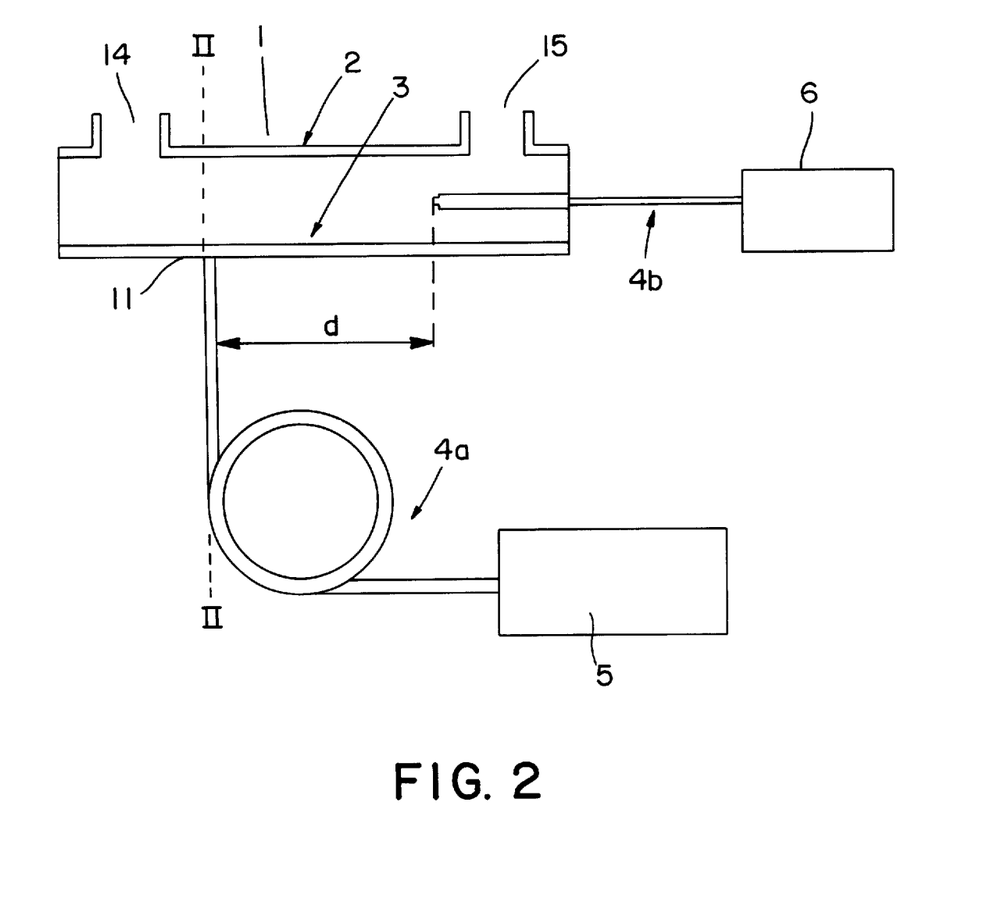
FIG. 2 schematically represents, on an enlarged scale, a liquid core optical sensor waveguide such as employed in the FIG. 1b implementation.
Figure 3A:
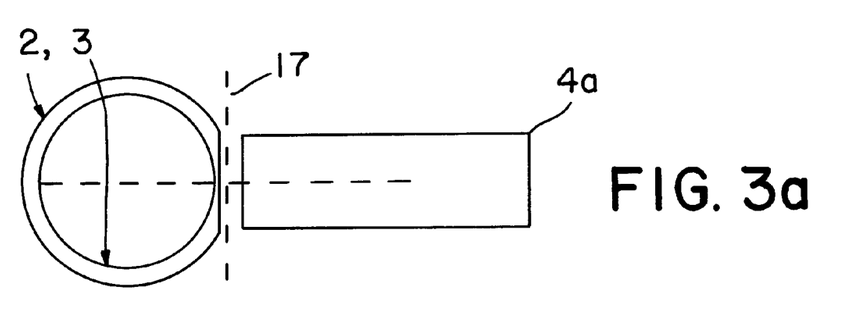
FIGS. 3a–3c are cross-sectional views taken along line II—II of FIG. 2.
Figure 3B:
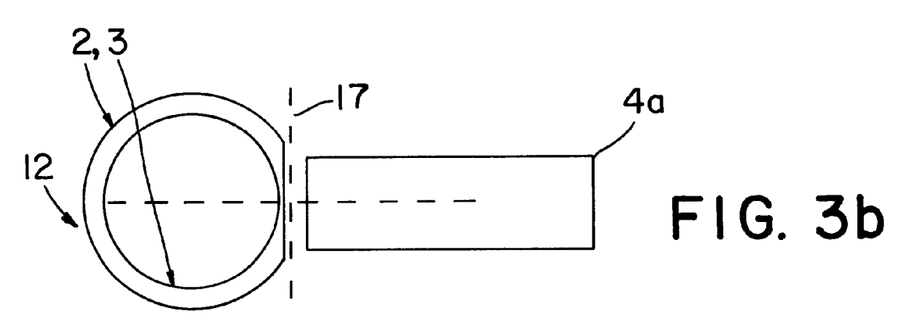
Figure 3C:
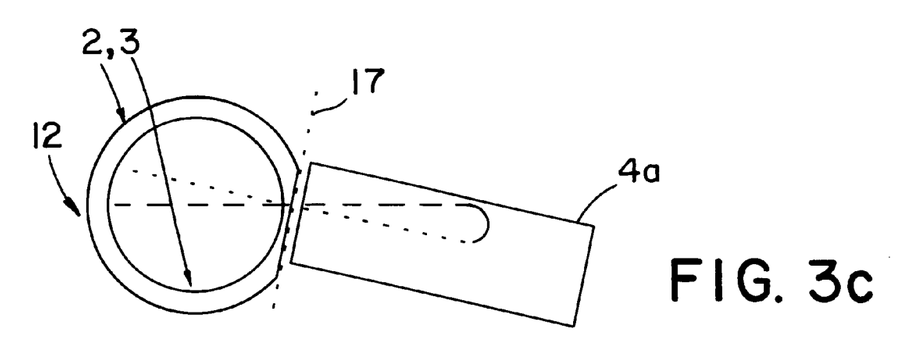

FIGS. 3a, 3b and 3c represent cross-sectional views of the liquid core waveguide 1 of FIGS. 1b and 2, FIG. 3 being a view taken along the line II—II of FIG. 2. It is first to be noted that an important aspect of the invention, particularly as it relates to transverse coupling of excitation light into the waveguide, is that there be no air gap between the end of optical fiber element 4a and an exterior surface of the waveguide. As depicted in FIG. 3, the exterior of capillary 2 is ground to provide a substantially flat, i.e., a polished, surface and the, end of the fiber optic element 4a is also ground, if necessary, so as to have a complementary shaped surface. This permits the establishment of a polished interface 17. In the arrangements of FIGS. 3a and 3b, the grinding of the exterior of the capillary 2 is done in such a manner that the axis of the fiber optic element 4a will, within manufacturing tolerances, intersect the longitudinal axis of the waveguide and the interface 17 will thus be tangential. In the arrangement of FIG. 3c, the grinding of the exterior of the capillary 2 is done at an angle, i.e., the plain of interface 17 is skewed with respect to that of the other depicted embodiments and the axes of the waveguide and the fiber optic element 4 do not intersect. The arrangement of FIG. 3c results in increased reflection of the excitation light within the waveguide and, accordingly, results in a device with increased sensitivity and an increased detection limit. In the arrangement of FIG. 3b, a reflective outer coating 12 is provided on the exterior of the waveguide in the interest of promoting excitation light reflection and, thereby, increasing sensitivity. The outer coating 12 is removed only at the interface 17 where light is coupled transversely into the capillary 2.

FIG. 3 is, of course, a schematic showing. In actual practice, there are three arrangements for ensuring the elimination of an air gap between the end of the fiber optic element 4a and the polished planar surface formed on the capillary 2 of the waveguide. Firstly, the components may be clamped together. Secondly, the region where the interface 17 is to be established may be cut out in a shape complementary to the shape of the end of fiber optic element 4a, i.e., a blind hole-type receiver may be formed, and the two components will be press fit together. Finally, the two components may be permanently bonded together by means of a light transparent adhesive. The use of an adhesive is recommended only if the wavelength of the excitation light will be in excess of 300 nm.

Figure 4A:
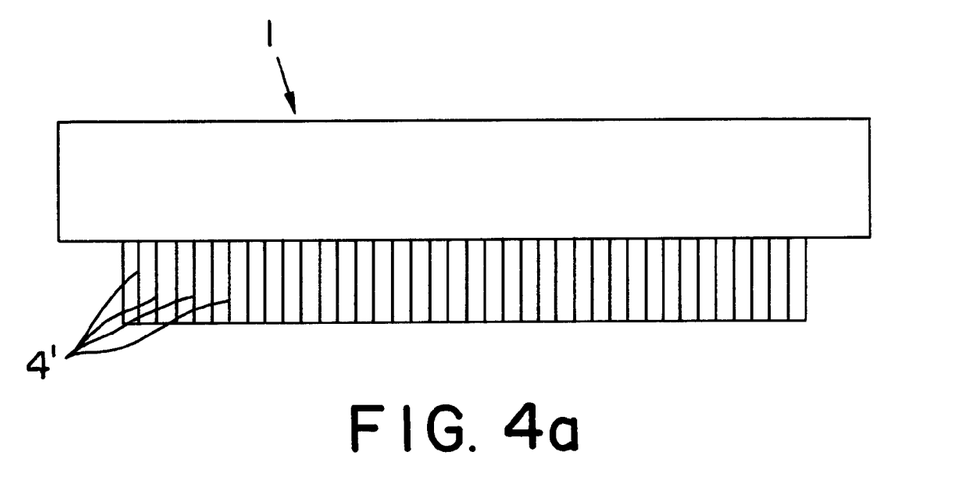
FIGS. 4a and 4b schematically represent an alternative hollow optical waveguide sensor in accordance with the invention, the sensor of FIG. 4a and 4b utilizing a linear array of optical fibers for coupling excitation light into the waveguide.
Figure 4B:
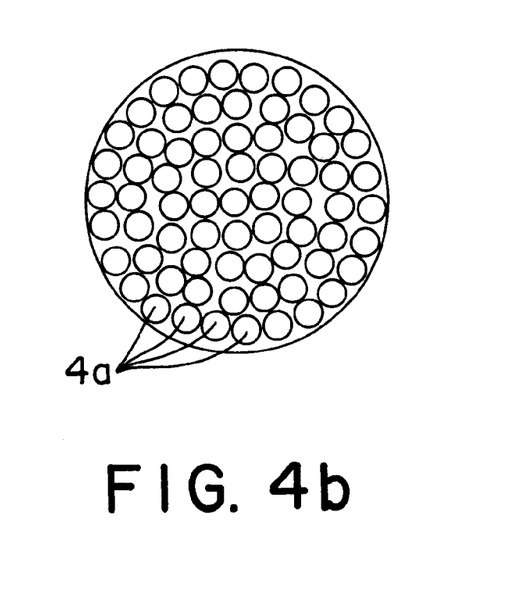

Referring now to FIGS. 4a and 4b, a further embodiment of a hollow optical waveguide in accordance with the invention is shown schematically. In the FIGS. 4a and 4b arrangement, the fiber optic element 4a comprises a bundle of individual fibers 4'. In order to increase the active optical path length of the excitation light, the individual fibers at the discharge end of element 4a are spread out to define a linear array which extends along the length of the waveguide. The ends of the individual fibers 4' are mated to the exterior of the capillary 2 of waveguide 1 using one of the techniques of FIG. 3. The FIGS. 4a and 4b arrangement allows different settings for coupling areas and, indeed, the light input to the individual fibers can be controlled to modulate the intensity of the excitation light. Also, the input end of the bundle of fibers 4a can be formed so as to better mate with the light source. For example, it is known that Excimer lasers have a rectangular coupling area.

Figure 5A:
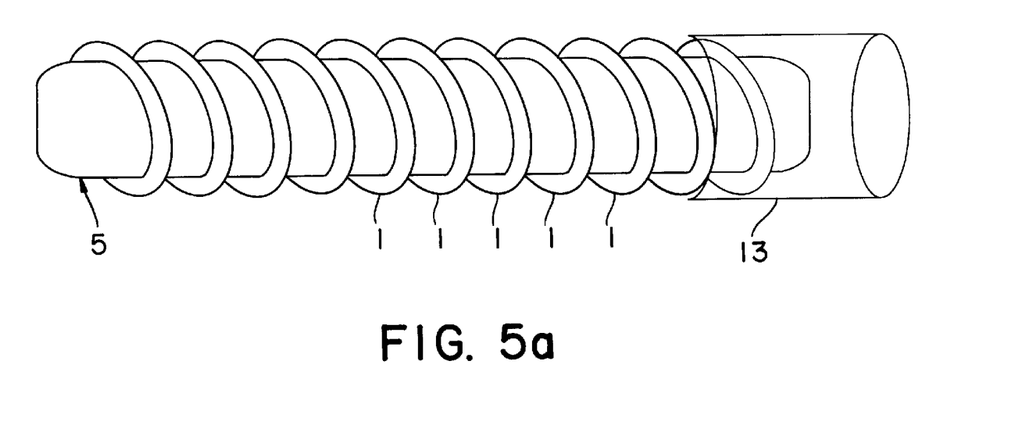
FIGS. 5a and 5b are each a schematic illustration of another embodiment of a hollow optical waveguide sensor in accordance with the invention.
Figure 5B:
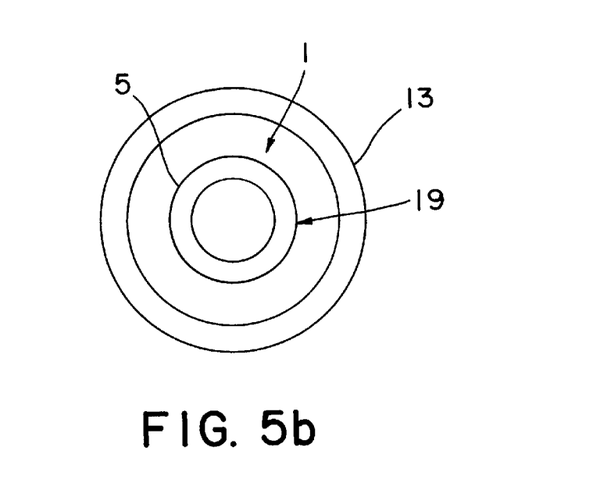

In the embodiment of FIGS. 5a and 5b, the hollow optical waveguide 1 is constructed so as to be flexible and the waveguide is then wrapped around an elongated light source 5. A flexible liquid core waveguide can be fabricated from Teflon AF tubing or from a flexible thin-walled capillary having an internal coating of Teflon AF. It should be noted that Teflon AF is a UV transparent material.

Continuing to discuss the FIGS. 5a and 5b embodiment, an external reflector 13 may be placed about the spiral wound waveguide 1 to increase the usable analysis light in the absorption mode and to achieve multiple passes of the excitation light through the waveguide core liquid in a fluorescence mode of operation. The reflective coating 13 also has the advantage of reducing interference caused by stray light. Additionally, the bar-formed lamp 5 can be provided with a fluorescent layer 19 in the interest of adapting the sensor to the light spectrum necessary for an absorption measurement on a detectable analyte, i.e., the apparatus can be used simultaneously for measurement of absorption and generated fluorescence.

While preferred embodiments have been shown and described, various modifications and substitutions may be made thereto without departing from the spirit and scope of the invention. By way of example, it is possible to employ, for the waveguide 1, an optically clear capillary having an external coating of amorphous fluorinated polymer rather than an internal coating as described herein. Also, while absorption and fluorescence measurements have been discussed in detail, the invention has applicability to measurement of Raman scattering. Accordingly, it is to be understood that the present invention has been described by way of illustration and not limitation.

What is claimed is:

1. Apparatus for optical trace analysis in an aqueous solution comprising:

a liquid core optical waveguide, said waveguide comprising an optically clear capillary having a hollow core region, said core region having a longitudinal axis, said waveguide having a layer comprised of an amorphous fluorinated polymer, said layer being coaxial with said core region, said polymer having an index of refraction which is less than the refractive index of the liquid to be delivered to the core region of the waveguide, said waveguide having first and second ends and an exterior side surface extending longitudinally between said ends;

a light source, the output frequency of said source being selected to cause the apparatus to function in a predetermined measurement mode;

means for transmitting light from said source into the core region of the waveguide, said transmitting means comprising at least a first optical fiber, said first optical fiber having a discharge end coupled to the exterior side surface of said waveguide and the light from said source passes through said first optical fiber into said core region without traversing an air gap;

means for collecting light in the core region of the waveguide and coupling the collected light out of the waveguide, said collecting means comprising at least a second optical fiber, said second optical fiber having a collection end;

means for analyzing the light coupled out of said waveguide by said collecting means; and means for delivering a liquid solvent to said waveguide core region.

2. The apparatus of claim 1 wherein said first optical fiber comprises a hydrogen doped fused silica fiber and the wavelength of the light provided by said source is in the range of 180 nm to 1050 nm.

3. The apparatus of claim 1 wherein said apparatus measures fluorescent light emitted by dissolved materials in a solvent and the light from said source passes into the waveguide core region to excite the emission of fluorescent light.

4. The apparatus of claim 3 wherein said waveguide is provided with a flat surface portion on said exterior side surface thereof and the end of said first optical fiber is in registration with said flat surface portion.

5. The apparatus of claim 4 wherein said light transmitting means comprises a plurality of additional optical fibers having their discharge ends linearly arranged next to each other along the longitudinal axis of the liquid core waveguide.

6. The apparatus of claim 4, wherein said first optical fiber has a second longitudinal axis and said flat surface portion is arranged such that said second longitudinal axis does not intersect with the longitudinal axis of said liquid core waveguide.

7. The apparatus of claim 1 further comprising discharge conduit means for controllably allowing fluid to flow out of said waveguide core region, said discharge conduit means being displaced from said solvent delivering means, said discharge conduit means being provided with a flow control valve whereby the flow of fluid through said waveguide core is selectively stopped during measurements.

8. The apparatus of claim 7 wherein said discharge end of said light transmitting means and said collection end of said collecting means are spatially displaced along said waveguide core axis and the distance between said transmitting and collecting means ends is less than the distance between said solvent delivering means and said discharge conduit means, both of said transmitting and collecting means ends being located at a point along the length of said waveguide where the flow of solvent within said waveguide is laminar.

9. The apparatus of claim 1 further comprising a reflector surrounding said waveguide.

10. The apparatus of claim 1 wherein said capillary has an inner diameter in the range of 100 to 600 $\mu$m.

11. An apparatus for measuring fluorescent light emitted by dissolved materials in a solvent, said apparatus comprising:

a liquid core optical waveguide having a hollow core region defining a longitudinal axis and having a longitudinally extending exterior side surface;

a light source, the output frequency of said source being selected to cause the apparatus to function in a predetermined measurement mode;

means for transmitting light from said source into the core region of the waveguide, said transmitting means comprising at least a first optical fiber, said first optical fiber having a discharge end coupled to said exterior side surface of said waveguide, the light from said source passing into the waveguide core region without traversing an air gap to excite the emission of fluorescent light;

means for collecting light in the core region of the waveguide and coupling the collected light out of the waveguide, said collecting means comprising at least a second optical fiber, said second optical fiber having a collection end; and means for delivering a liquid solvent to said waveguide core region.

12. The apparatus of claim 11 further comprising discharge conduit means for controllably allowing fluid to flow out of said waveguide core region, said discharge conduit means being displaced from said solvent delivering means, said discharge conduit means being provided with a flow control valve whereby the flow of fluid through said waveguide core is selectively stopped during measurements.

13. The apparatus of claim 12 wherein said discharge end of said light transmitting means and said collection end of said collecting means are spatially displaced along said waveguide core axis and the distance between said transmitting and collecting means ends is less than the distance between said solvent delivering means and said discharge conduit means, both of said transmitting and collecting means ends being located at a point along the length of said waveguide where the flow of solvent within said waveguide is laminar.

14. The apparatus of claim 11, wherein said waveguide is provided with a flat surface portion on said exterior side surface thereof and the end of said first optical fiber is in registration with said flat surface portion.

15. The apparatus of claim 14 wherein said light transmitting means comprises a plurality of additional optical fibers having their discharge ends linearly arranged next to each other along the longitudinal axis of the liquid core waveguide.

16. The apparatus of claim 14, wherein said first optical fiber has a second longitudinal axis and said flat surface portion is arranged such that said second longitudinal axis does not intersect with the longitudinal axis of said liquid core waveguide.

* * * * *

UNITED STATES PATENT AND TRADEMARK OFFICE
CERTIFICATE OF CORRECTION

PATENT NO. : 6,385,380 B1
DATED : May 7, 2002
INVENTOR(S) : Klein et al.

It is certified that error appears in the above-identified patent and that said Letters Patent is hereby corrected as shown below:

<u>Title page,</u>
Item [12], delete "Friedrich et al" and insert -- Klein et al --.

Item [75], delete "Karl Friedrich" and insert -- Karl F. Klein --.

Signed and Sealed this

Fifth Day of November, 2002

Attest:

Attesting Officer

JAMES E. ROGAN
*Director of the United States Patent and Trademark Office*